United States Patent
Huang et al.

(10) Patent No.: US 11,839,590 B2
(45) Date of Patent: Dec. 12, 2023

(54) FLURBIPROFEN AXETIL EMULSION FOR INJECTION AND PREPARATION METHOD THEREOF

(71) Applicant: Grand life science (wuhan) co., LTD, Wuhan (CN)

(72) Inventors: Ling Huang, WuHan (CN); Xiaohua Zhang, WuHan (CN); Jinchun Song, WuHan (CN); Lei Yin, WuHan (CN)

(73) Assignee: Grand life science (wuhan) co., LTD, Wuhan (CN)

( * ) Notice: Subject to any disclaimer, the term of this patent is extended or adjusted under 35 U.S.C. 154(b) by 52 days.

(21) Appl. No.: 16/652,388

(22) PCT Filed: Jan. 21, 2019

(86) PCT No.: PCT/CN2019/072562
§ 371 (c)(1),
(2) Date: Mar. 30, 2020

(87) PCT Pub. No.: WO2020/073559
PCT Pub. Date: Apr. 16, 2020

(65) Prior Publication Data
US 2021/0220303 A1    Jul. 22, 2021

(30) Foreign Application Priority Data
Oct. 10, 2018   (CN) .......................... 201811175197.7

(51) Int. Cl.
*A61K 31/192*    (2006.01)
*A61K 9/00*    (2006.01)
*A61K 9/107*    (2006.01)
*A61K 47/10*    (2017.01)
*A61K 47/24*    (2006.01)
*A61K 47/26*    (2006.01)

(52) U.S. Cl.
CPC .......... *A61K 31/192* (2013.01); *A61K 9/0019* (2013.01); *A61K 9/107* (2013.01); *A61K 47/10* (2013.01); *A61K 47/24* (2013.01); *A61K 47/26* (2013.01)

(58) Field of Classification Search
CPC ........ A61K 47/26; A61K 47/24; A61K 47/10; A61K 9/107; A61K 9/0019; A61K 31/192
See application file for complete search history.

(56) References Cited

U.S. PATENT DOCUMENTS

2006/0134145 A1*  6/2006  Matsuda .............. A61K 9/0019
                                                                        514/731

FOREIGN PATENT DOCUMENTS

| CN | 102988291 B | | 5/2014 |
|----|----|----|----|
| CN | 104434901 B | | 3/2016 |
| CN | 104188905 B | | 8/2016 |
| CN | 104922065 B | | 1/2018 |
| EP | 0298293 | * | 1/1989 |
| TW | 201828935 | * | 8/2018 |

OTHER PUBLICATIONS

Yohei, TW 201828935, English machine translation obtained on Oct. 14, 2022. (Year: 2022).*
Sommermeyer et al., EP 0298293, English machine translation obtained on Oct. 14, 2022. (Year: 2022).*

* cited by examiner

*Primary Examiner* — Genevieve S Alley
(74) *Attorney, Agent, or Firm* — Knobbe, Martens, Olson & Bear, LLP

(57) ABSTRACT

A flurbiprofen axetil emulsion for injection can be prepared by specific stepwise addition of an oil phase to a water phase with shear mixing under the protection of nitrogen gas to obtain an emulsion. The oil phase includes flurbiprofen axetil, an oil phase solvent, an emulsifier, and a stabilizer, and the water phase includes water for injection and/or an osmotic pressure regulator. In the presence of a stabilizer in the oil phase, the emulsion can improve the emulsification effect by using the stepwise emulsifying technique for the oil phase, so that the obtained flurbiprofen axetil emulsion for injection has more uniform particle size, higher drug entrapment efficiency, and better targeting of the drug to the wounded tissue.

11 Claims, 4 Drawing Sheets

FLURBIPROFEN AXETIL EMULSION FOR INJECTION AND PREPARATION METHOD THEREOF

CROSS-REFERENCE TO RELATED APPLICATION

This application is the U.S. National Phase under 35 U.S.C. § 371 of International Application No. PCT/CN2019/072562, filed Jan. 21, 2019, designating the U.S., which claims priority to the Chinese Patent Application No. 201811175197.7, filed on Oct. 10, 2018, the entire content of which are incorporated herein by reference.

TECHNICAL FIELD

The present invention relates to the field of pharmaceutical formulations, specifically, to a flurbiprofen axetil emulsion for injection and a preparation method thereof.

BACKGROUND ART

Flurbiprofen axetil is a prodrug of flurbiprofen, which is used for postoperative and cancer analgesia. Flurbiprofen axetil emulsion for injection is a new type of targeted analgesic with fat emulsion (also known as lipid microspheres) as a carrier. After emulsion particles enter the body and target to the wound and tumor sites, flurbiprofen axetil is released from the emulsion particles, and is rapidly hydrolyzed by carboxyesterase to form flurbiprofen. Flurbiprofen inhibits cyclooxygenase in the process of arachidonic acid metabolism, thereby inhibiting the synthesis of prostaglandins to exert analgesic effects. This drug-loaded emulsion has stronger efficacy, faster onset, longer duration, and is less likely to cause adverse reactions such as gastric mucosal damage, and has been widely used in clinical practice.

The preparation method of flurbiprofen axetil emulsion for injection is complicated, the production reproducibility is poor, and there are problems such as poor stability during commercial production and storage. Flurbiprofen axetil emulsion for injection may be unstable or even demulsified during high temperature sterilization or storage, which may affect its stability and safety. Meanwhile, its main drug flurbiprofen axetil is easily degraded to produce impurities such as flurbiprofen which has vascular irritation. In addition, lipid substances are easily oxidized to produce aldehydes and ketones, affecting clinical safety. In order to improve the stability of emulsion, the mixing process of raw materials and excipients was carried out at normal temperature in the patent CN102988291B; Vitamin E was added in the patent CN104434901B; an emulsifier which contains a small amount of phosphatidylcholine, phosphatidylethanolamine, and phosphatidylglycerol was added in the patent CN104922065B; and polyethylene glycol-distearylethanolamine and vitamin E were added in the patent CN104188905B to improve the stability of the flurbiprofen axetil emulsion for injection. The above technologies improve the stability of flurbiprofen axetil emulsion for injection to a certain extent, and increase the safety of clinical use. However, these technologies ignore the key indicator-drug entrapment efficiency that affects the in vitro-in vivo correlation of flurbiprofen axetil emulsion for injection, which will affect the targeting effect of the drug into the body, which is unfavorable to the effectiveness of the drug.

In order to meet the medical requirements of the general patients, a more advanced technology is needed to realize the industrialization of flurbiprofen axetil emulsion for injection with a more stable quality to make up for the shortcomings of the prior art.

SUMMARY OF THE INVENTION

The object of the present invention is to provide a flurbiprofen axetil emulsion for injection with good in vitro-in vivo correlation and preparation method thereof.

A first purpose of the present invention is to provide a preparation method of a flurbiprofen axetil emulsion for injection. The method comprises the following steps:

under the protection of nitrogen gas, an oil phase is added to a water phase in a stepwise manner to perform shear mixing to obtain an initial emulsion;

the stepwise manner is specifically as follows:

40 wt % to 60 wt % of an oil phase based on the total oil phase is added to a water phase to perform shear mixing for 10 min to 30 min to obtain a crude emulsion A;

20 wt % to 30 wt % of an oil phase based on the total oil phase is added to the crude emulsion A to perform shear mixing for 10 min to 30 min to obtain a crude emulsion B; and the crude emulsion B is mixed with the rest of the total oil phase to perform shear mixing for 10 min to 30 min;

the oil phase includes flurbiprofen axetil, an oil phase solvent, an emulsifier, and a stabilizer, and the water phase includes water for injection and/or an osmotic pressure regulator.

In the presence of a stabilizer in the oil phase, the present invention can improve the emulsification effect and increase the stability of the initial emulsion by using the above stepwise emulsifying technique of the oil phase, so that the obtained flurbiprofen axetil emulsion for injection has more uniform particle size, higher drug entrapment efficiency, and better targeting of the drug to the wounded tissue.

In a preferred embodiment of the present invention, the stepwise manner is specifically as follows:

45 wt % to 55 wt % of an oil phase based on the total oil phase is added to a water phase to perform shear mixing for 10 min to 20 min to obtain a crude emulsion A;

20 wt % to 30 wt % of an oil phase based on the total oil phase is added to the crude emulsion A to perform shear mixing for 10 min to 20 min to obtain a crude emulsion B; and the crude emulsion B is mixed with the rest of the total oil phase to perform shear mixing for 20 min to 30 min.

In a preferred embodiment of the present invention, the speed of the shear mixing in the stepwise manner is 4000 rpm to 10000 rpm.

In a preferred embodiment of the present invention, in order to improve the uniformity of the emulsion particles and improve the emulsification effect of the crude emulsion, the stepwise manner may specifically be:

45 wt % to 55 wt % of an oil phase based on the total oil phase is added to a water phase to perform shear mixing at 4000 rpm to 6000 rpm for 10 min to 20 min to obtain a crude emulsion A;

20 wt % to 30 wt % of an oil phase based on the total oil phase is added to the crude emulsion A to perform shear mixing at 6000 rpm to 8000 rpm for 10 min to 20 min to obtain a crude emulsion B;

then the crude emulsion B is mixed with the rest of the total oil phase to perform shear mixing at 8000 rpm to 10000 rpm for 20 min to 30 min.

In a preferred embodiment of the present invention, the stepwise manner may specifically be as follows:

45 wt % to 55 wt % of an oil phase based on the total oil phase is added to a water phase to perform shear mixing at 5000 rpm to 6000 rpm for 10 min to 20 min to obtain a crude emulsion A;

20 wt % to 30 wt % of an oil phase based on the total oil phase is added to the crude emulsion A to perform shear mixing at 7000 rpm to 8000 rpm for 10 min to 20 min to obtain a crude emulsion B;

then the crude emulsion B is mixed with the rest of the total oil phase to perform shear mixing at 9000 rpm to 10000 rpm for 20 min to 30 min.

In a preferred embodiment of the present invention, the stepwise manner may specifically be as follows:

45 wt % to 55 wt % of an oil phase based on the total oil phase is added to a water phase to perform shear mixing at 5000 rpm to 6000 rpm for 10 min to 13 min to obtain a crude emulsion A;

20 wt % to 30 wt % of an oil phase based on the total oil phase is added to the crude emulsion A to perform shear mixing at 7000 rpm to 8000 rpm for 15 min to 20 min to obtain a crude emulsion B;

then the crude emulsion B is mixed with the rest of the total oil phase with shear mixing at 9000 rpm to 10000 rpm for 25 min to 30 min.

In an embodiment of the present invention, flurbiprofen axetil, an oil phase solvent, an emulsifier, and a stabilizer can be stirred and mixed at a temperature of 60° C. to 75° C. for 10 to 30 min under a nitrogen gas atmosphere to obtain a uniform oil phase.

In a preferred embodiment of the present invention, the stabilizer is one or two selected from dioleoylphosphatidylserine, dipalmitoylphosphatidic acid, and sphingomyelin, preferably dioleoylphosphatidylserine.

The stabilizer is added in an amount such that the flurbiprofen axetil emulsion for injection includes 0.01% to 0.1% of the stabilizer, wherein, "%" means w/v.

In a preferred embodiment of the present invention, the oil phase solvent is one or more selected from refined soybean oil, olive oil, and medium-chain triglycerides. In a specific embodiment, the oil phase solvent may be refined soybean oil.

In a preferred embodiment of the present invention, the emulsifier is one or two selected from egg yolk lecithin, soybean lecithin, and polyethylene glycol glyceryl stearate, preferably egg yolk lecithin.

In a preferred embodiment of the present invention, the above-mentioned flurbiprofen axetil emulsion for injection includes the following components: 1% to 2% of flurbiprofen axetil, 8% to 12% of an oil phase solvent, 1.0% to 1.5% of an emulsifier, and 0.01% to 0.1% of a stabilizer, and the rest is water for injection, wherein, "%" means w/v.

In a preferred embodiment of the present invention, an osmotic pressure regulator may be further included in the water phase, and the osmotic pressure regulator is added in an amount such that the flurbiprofen axetil emulsion for injection includes 2.0% to 3.0% of the osmotic pressure regulator, wherein, "%" means w/v.

The osmotic pressure regulator is preferably one or two selected from glycerol, sucrose, and mannitol.

When the osmotic pressure regulator is included in the water phase, the osmotic pressure regulator and water for injection can be stirred and mixed uniformly to obtain the water phase, which is heated to 60° C. to 75° C. for later use.

In a preferred embodiment of the present invention, the above-mentioned flurbiprofen axetil emulsion for injection includes the following components: 1% to 2% of flurbiprofen axetil, 8% to 12% of an oil phase solvent, 1.0% to 1.5% of an emulsifier, 0.01% to 0.1% of a stabilizer, and 2.0% to 3.0% of an osmotic pressure regulator, and the rest is water for injection, wherein, "%" means w/v.

In a preferred embodiment of the present invention, the preparation method of flurbiprofen axetil emulsion for injection may include the following steps:

under the protection of nitrogen gas, an oil phase is added to a water phase in a stepwise manner to perform shear mixing to obtain an initial emulsion;

the stepwise manner is specifically as follows:

40 wt % to 60 wt % of an oil phase based on the total oil phase is added to a water phase to perform shear mixing for 10 min to 30 min to obtain a crude emulsion A;

20 wt % to 30 wt % of an oil phase based on the total oil phase is added to the crude emulsion A to perform shear mixing for 10 min to 30 min to obtain a crude emulsion B; and the crude emulsion B is mixed with the rest of the total oil phase to perform shear mixing for 10 min to 30 min;

the oil phase includes flurbiprofen axetil, refined soybean oil, egg yolk lecithin, and dioleylphosphatidylserine, and the water phase includes water for injection and glycerol.

In a specific embodiment of the present invention, the obtained initial emulsion can be processed by a conventional method to obtain a flurbiprofen axetil emulsion for injection. Preferably, the method may include adjusting pH of the initial emulsion to 6.0 to 7.0, and then homogenizing for 3 to 5 times to obtain a semi-finished product; and then subjecting the obtained semi-finished product to filtration, filling, sealing and sterilizing to obtain the flurbiprofen axetil emulsion for injection. The homogenizing pressure is preferably 60 Mpa to 100 Mpa, and the homogenizing temperature is preferably 10° C. to 40° C. Rotating water bath sterilization process may be used for sterilization to ensure that the FO value is greater than 12. The pH of the initial emulsion can be adjusted to 6.0 to 7.0 with a pH adjuster. The pH adjuster may be one or two selected from sodium hydroxide, potassium hydroxide, disodium hydrogen phosphate, dipotassium hydrogen phosphate, hydrochloric acid, and citric acid.

Another purpose of the present invention is to provide a flurbiprofen axetil emulsion for injection obtained by the above preparation method.

After the flurbiprofen axetil emulsion for injection obtained by the present invention was injected into a rat, there was no drug accumulation in the main organs of the rat such as heart, liver, spleen, lung, kidney, and muscle. Compared with the normal muscle, the wounded muscles had higher drug concentrations at different time points after administration. The flurbiprofen axetil emulsion for injection obtained by the present invention has stronger targeting to wounded tissues and it contributes to improve the therapeutic effect of the drug.

Compared with the prior art, the present invention has the following beneficial effects:
(1) In the present invention, by adding a stabilizer (preferably dioleoylphosphatidylserine, dipalmitoylphosphatidic acid, or sphingomyelin) to the oil phase and using the stepwise emulsifying technique for the oil phase, the emulsification effect can be improved and the stability of the initial emulsion can be increased.
(2) By using the preparation method of the present invention, the emulsification efficiency of the initial emulsion can be improved, the resistance to high-pressure homogenization can be reduced, the emulsion can be more easily formed, and the energy consumption of equipment can be reduced, thereby facilitating commercial production.

(3) The emulsion particles of the flurbiprofen axetil emulsion for injection obtained by the preparation method of the present invention have more uniform particle size, and the drug entrapment efficiency is improved to further reduce the degradation of free drugs and the oxidation of oily auxiliary materials during sterilization and storage, thereby improving the targeting effect of the drug to ensure the effectiveness and safety of clinical use.

SPECIFIC MODES FOR CARRYING OUT THE EMBODIMENTS

Figure 1:
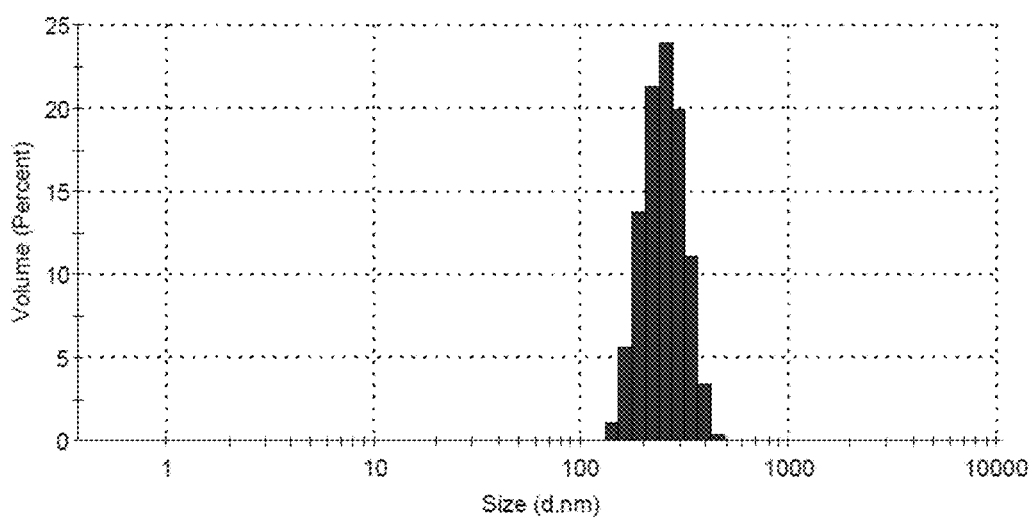
FIG. 1 is a particle size distribution diagram of the flurbiprofen axetil emulsion for injection provided in Example 1 of the present invention.

Specific modes for carrying out the embodiments of the present invention will be further described in detail in combination with Examples. The following Examples are intended to illustrate the present invention, but are not intended to limit to the scope of the present invention.

The raw materials used in the present invention are all commercially available, and the reagents used in the Examples of the present invention are all chemically pure.

Example 1

The present Example provides a flurbiprofen axetil emulsion for injection, the formulation of which was as follows:
flurbiprofen axetil 10 g
refined soybean oil 100 g
egg yolk lecithin 12 g
dioleoylphosphatidylserine 0.1 g
glycerol 22.5 g
sodium hydroxide, hydrochloric acid appropriate amount
water for injection added to 1000 ml
The preparation method was as follows:
(1) the formulation amount of flurbiprofen axetil, refined soybean oil, egg yolk lecithin, and dioleoylphosphatidylserine were stirred and mixed at 60° C. for 30 min under a nitrogen gas atmosphere to obtain a uniform oil phase (122.1 g) for later use;
(2) the formulation amount of glycerol and water for injection were stirred and mixed uniformly and the mixture was heated to 60° C. for later use;
(3) 48.8 g of the oil phase of step (1) was shear mixed with the water phase of step (2) at 4000 rpm for 10 min under the protection of nitrogen gas to obtain a crude emulsion A; the crude emulsion A was shear mixed with 36.6 g of the oil phase of step (1) at 6000 rpm for 10 min to obtain a crude emulsion B; the crude emulsion B was shear mixed with 36.6 g of the oil phase of step (1) at 8000 rpm for 20 min to obtain an initial emulsion;
(4) pH of the initial emulsion obtained in step (3) was adjusted to 6.0 to 7.0, and then the initial emulsion was homogenized for 3 to 5 times under high pressure of 60 Mpa and a homogenizing temperature of 10 to 40° C. to obtain a semi-finished product; and
(5) the semi-finished product obtained in step (4) was filtered, filled and sealed, and sterilized by rotating water bath at 121° C. for 12 min to obtain a flurbiprofen axetil emulsion for injection.

Example 2

The present Example provides a flurbiprofen axetil emulsion for injection, the formulation of which was as follows:
flurbiprofen axetil 20 g
olive oil 120 g
soy lecithin 15 g
dipalmitoylphosphatidic acid 1.0 g
sucrose 30 g
citric acid, sodium hydroxide appropriate amount
water for injection added to 1000 ml
The preparation method was as follows:
(1) the formulation amount of flurbiprofen axetil, olive oil, soy lecithin, and dipalmitoylphosphatidic acid were stirred and mixed at 65° C. for 20 min under a nitrogen gas atmosphere to obtain a uniform oil phase (156 g) for later use;
(2) the formulation amount of sucrose and water for injection were stirred and mixed uniformly and the mixture was heated to 65° C. for later use;
(3) 78 g of the oil phase of step (1) was shear mixed with the water phase of step (2) at 5000 rpm for 15 min under the protection of nitrogen gas to obtain a crude emulsion A; the crude emulsion A was shear mixed with 39 g of the oil phase of step (1) at 7000 rpm for 15 min to obtain a crude emulsion B; the crude emulsion B was shear mixed with 39 g of the oil phase of step (1) at 9000 rpm for 30 min to obtain an initial emulsion;
(4) pH of the initial emulsion obtained in step (3) was adjusted to 6.0 to 7.0, and then the initial emulsion was homogenized for 3 to 5 times under high pressure of 70 Mpa and a homogenizing temperature of 10 to 40° C. to obtain a semi-finished product; and
(5) the semi-finished product obtained in step (4) was filtered, filled and sealed, and sterilized by rotating water bath at 124° C. for 8 min to obtain a flurbiprofen axetil emulsion for injection.

Example 3

The present Example provides a flurbiprofen axetil emulsion for injection, the formulation of which was as follows:

flurbiprofen axetil 15 g
medium-chain triglycerides 50 g
refined soybean oil 50 g
polyethylene glycol glyceryl stearate 10 g
sphingomyelin 0.8 g
mannitol 22.5 g
disodium hydrogen phosphate, citric acid appropriate amount
water for injection added to 1000 ml The preparation method was as follows:
(1) the formulation amount of flurbiprofen axetil, medium-chain triglycerides, refined soybean oil, polyethylene glycol glyceryl stearate, and sphingomyelin were stirred and mixed at 70° C. for 15 min under a nitrogen gas atmosphere to obtain a uniform oil phase (125.8 g) for later use;
(2) the formulation amount of mannitol and water for injection were stirred and mixed uniformly and the mixture was heated to 70° C. for later use;
(3) 75.5 g of the oil phase of step (1) was shear mixed with the water phase of step (2) at 6000 rpm for 20 min under the protection of nitrogen gas to obtain a crude emulsion A; the crude emulsion A was shear mixed with 25 g of the oil phase of step (1) at 8000 rpm for 20 min to obtain a crude emulsion B; the crude emulsion B was shear mixed with 25 g of the oil phase of step (1) at 10000 rpm for 30 min to obtain an initial emulsion;
(4) pH of the initial emulsion obtained in step (3) was adjusted to 6.0 to 7.0, and then the initial emulsion was homogenized for 3 to 5 times under high pressure of 80 Mpa and a homogenizing temperature of 10 to 40° C. to obtain a semi-finished product; and
(5) the semi-finished product obtained in step (4) was filtered, filled and sealed, and sterilized by rotating water bath at 127° C. for 5 min to obtain a flurbiprofen axetil emulsion for injection.

Example 4

The present Example provides a flurbiprofen axetil emulsion for injection, the formulation of which was as follows:
flurbiprofen axetil 10 g
medium-chain triglycerides 25 g
olive oil 75 g
soy lecithin 12 g
dipalmitoylphosphatidic acid 0.5 g
glycerol 25 g
sodium dihydrogen phosphate+dilute hydrochloric acid appropriate amount
water for injection added to 1000 ml The preparation method was as follows:
(1) the formulation amount of flurbiprofen axetil, medium-chain triglycerides, olive oil, soy lecithin, and dipalmitoylphosphatidic acid were stirred and mixed at 75° C. for 10 min under a nitrogen gas atmosphere to obtain a uniform oil phase (122.5 g) for later use;
(2) the formulation amount of glycerol and water for injection were stirred and mixed uniformly and the mixture was heated to 75° C. for later use;
(3) 61.2 g of the oil phase of step (1) was shear mixed with the water phase of step (2) at 5000 rpm for 20 min under the protection of nitrogen gas to obtain a crude emulsion A; the crude emulsion A was shear mixed with 30.6 g of the oil phase of step (1) at 6000 rpm for 20 min to obtain a crude emulsion B; the crude emulsion B was shear mixed with 30.6 g of the oil phase of step (1) at 8000 rpm for 30 min to obtain an initial emulsion;
(4) pH of the initial emulsion obtained in step (3) was adjusted to 6.0 to 7.0, and then the initial emulsion was homogenized for 3 to 5 times under high pressure of 100 Mpa and a homogenizing temperature of 10 to 40° C. to obtain a semi-finished product; and
(5) the semi-finished product obtained in step (4) was filtered, filled and sealed, and sterilized by rotating water bath at 127° C. for 5 min to obtain a flurbiprofen axetil emulsion for injection.

Example 5

The present Example provides a flurbiprofen axetil emulsion for injection, the formulation of which was as follows:
flurbiprofen axetil 10 g
refined soybean oil 80 g
egg yolk lecithin 10 g
dioleoylphosphatidylserine 0.2 g
sucrose 22.5 g
dipotassium hydrogen phosphate, citric acid appropriate amount
water for injection added to 1000 ml The preparation method was as follows:
(1) the formulation amount of flurbiprofen axetil, refined soybean oil, egg yolk lecithin, and dioleoylphosphatidylserine were stirred and mixed at 75° C. for 15 min under a nitrogen gas atmosphere to obtain a uniform oil phase (100.2 g) for later use;
(2) the formulation amount of sucrose and water for injection were stirred and mixed uniformly and the mixture was heated to 75° C. for later use;
(3) 60.1 g of the oil phase of step (1) was shear mixed with the water phase of step (2) at 6000 rpm for 10 min under the protection of nitrogen gas to obtain a crude emulsion A; the crude emulsion A was shear mixed with 20 g of the oil phase of step (1) at 8000 rpm for 15 min to obtain a crude emulsion B; the crude emulsion B was shear mixed with 20 g of the oil phase of step (1) at 10000 rpm for 30 min to obtain an initial emulsion;
(4) pH of the initial emulsion obtained in step (3) was adjusted to 6.0 to 7.0, and then the initial emulsion was homogenized for 3 to 5 times under high pressure of 90 Mpa and a homogenizing temperature of 10 to 40° C. to obtain a semi-finished product; and
(5) the semi-finished product obtained in step (4) was filtered, filled and sealed, and sterilized by rotating water bath at 124° C. for 8 min to obtain a flurbiprofen axetil emulsion for injection.

Comparative Example 1

The present Comparative Example provides a flurbiprofen axetil emulsion for injection, the formulation of which was as follows:
flurbiprofen axetil 10 g
refined soybean oil 100 g
soy lecithin 12 g
glycerol 22.5 g
oleic acid 0.5 g
citric acid, sodium hydroxide appropriate amount
water for injection added to 1000 ml The preparation method was as follows:

The formulation amount of flurbiprofen axetil, refined soybean oil, soy lecithin and oleic acid were stirred and mixed at 65° C. for 30 min to form a clear oil solution. The formulation amount of glycerol and water for injection were stirred and mixed uniformly to obtain a water phase. The oil phase and the water phase were subjected to shear mixing at 8000 rpm for 30 min to obtain an initial emulsion. pH of the initial emulsion was adjusted to 6.0 to 7.0 with citric acid and sodium hydroxide. The initial emulsion was homogenized for 5 times under high pressure of 80 Mpa, then subjected to filtering, filling, sealing, and sterilizing by rotating water bath at 121° C. for 12 min to obtain a flurbiprofen axetil emulsion for injection.

Comparative Example 2

The present Comparative Example provides a flurbiprofen axetil emulsion for injection, the formulation of which was as follows:

flurbiprofen axetil 10 g
refined soybean oil 100 g
egg yolk lecithin 12 g
glycerol 12 g
dioleoylphosphatidylserine 1.0 g
citric acid, disodium hydrogen phosphate appropriate amount
water for injection added to 1000 ml The preparation method was as follows:

The formulation amount of flurbiprofen axetil, refined soybean oil, egg yolk lecithin and dioleoylphosphatidylserine were mixed at 70° C. under high-speed stirring to form a solution. The formulation amount of glycerol and water for injection were stirred and mixed uniformly at 70° C. to obtain a water phase. The oil phase and the water phase were stirred and mixed at 6000 rpm for 20 min to obtain an initial emulsion. pH of the initial emulsion was adjusted to 6.0 to 7.0 with citric acid and disodium hydrogen phosphate. The initial emulsion was homogenized for 5 times under high pressure of 80 Mpa, then subjected to filtering, filling, sealing, and sterilizing by rotating water bath at 121° C. for 12 min to obtain a flurbiprofen axetil emulsion for injection.

Comparative Example 3

The present Comparative Example provides a flurbiprofen axetil emulsion for injection, the formulation of which was as follows:

flurbiprofen axetil 10 g
refined soybean oil 100 g
polyethylene glycol glyceryl stearate 12 g
glycerol 22.5 g
citric acid, disodium hydrogen phosphate appropriate amount
water for injection added to 1000 ml The preparation method was as follows:

(1) the formulation amount of flurbiprofen axetil, refined soybean oil and polyethylene glycol glyceryl stearate were stirred and mixed at 75° C. to obtain a uniform oil phase (122 g) for later use;
(2) the formulation amount of glycerol and water for injection in appropriate amount were stirred and mixed uniformly and the mixture was heated to 75° C. for later use;
(3) 61 g of the oil phase of step (1) was shear mixed with the water phase of step (2) at 6000 rpm for 15 min under the protection of nitrogen gas to obtain a crude emulsion A; the crude emulsion A was shear mixed with 30 g of the oil phase of step (1) at 8000 rpm for 20 min to obtain a crude emulsion B; the crude emulsion B was shear mixed with 30 g of the oil phase of step (1) at 10000 rpm for 30 min to obtain an initial emulsion;
(4) pH of the initial emulsion obtained in step (3) was adjusted to 6.0 to 7.0, and then the initial emulsion was homogenized for 3 to 5 times under high pressure of 100 Mpa and a homogenizing temperature of 10 to 40° C. to obtain a semi-finished product; and
(5) the semi-finished product obtained in step (4) was filtered, filled and sealed, and sterilized by rotating water bath at 124° C. for 8 min to obtain a flurbiprofen axetil emulsion for injection.

In the following test examples, stability of the initial emulsion, physical and chemical properties, and entrapment efficiency of the flurbiprofen axetil emulsion for injection prepared above were determined, and the characteristics of the tissue distribution in vivo of the drug were determined by animal models.

Experimental Example 1: Stability Test of Initial Emulsion

The initial emulsions prepared in the steps (3) of Examples 1 to 5 and the initial emulsions prepared in Comparative Examples 1 to 3 were tested for the stability of initial emulsion: The stability constant (Ke) was used as an evaluation index. The stability constant of the initial emulsions were determined. The larger the Ke value, the worse the stability. The initial emulsions were placed at room temperature for 20 min, 30 min, 40 min or 60 min, respectively. The initial emulsions were observed to determine whether phenomena such as floating oil, demulsification, and oil-water phase separation appeared. Stability results of the initial emulsions were shown in Table 1.

Evaluation method of stability constant (Ke): $Ke=(A_0-A)/A \times 100\%$ $A_0$—absorbance of uncentrifuged emulsion diluent;
$A$—absorbance of emulsion diluent after centrifugation.

Determination method: 8 mL of an initial emulsion was taken into a 10 ml sharp-bottomed centrifuge tube, and was centrifuged at 1000 r·min$^{-1}$ for 5 min. A 1 ml graduated pipette was used to accurately measure out 0.5 ml of the sample at the bottom of the centrifuge tube into a 100 ml volumetric flask. The sample was diluted to the scale mark with distilled water and the volumetric flask was shaken evenly. The absorbance A at a wavelength of 500 nm in the visible region was measured with distilled water as a blank. The absorbance $A_0$ of the uncentrifuged initial emulsion was measured in the same way, and Ke was calculated. The results were shown in Table 1.

TABLE 1

Comparison of stability of initial emulsions

| | Ke | 20 min | 30 min | 40 min | 60 min |
|---|---|---|---|---|---|
| Example 1 | 0.27 | no obvious floating oil | no obvious floating oil | no obvious floating oil | slight floating oil |
| Example 2 | 0.28 | no obvious floating oil | no obvious floating oil | no obvious floating oil | slight floating oil |
| Example 3 | 0.37 | no obvious floating oil | no obvious floating oil | no obvious floating oil | slight floating oil |
| Example 4 | 0.18 | no obvious floating oil | no obvious floating oil | no obvious floating oil | slight floating oil |
| Example 5 | 0.15 | no obvious floating oil | no obvious floating oil | no obvious floating oil | slight floating oil |
| Comparative Example 1 | 0.63 | no obvious floating oil | slight floating oil | slight layer-separation | obvious layer-separation, demulsification |
| Comparative Example 2 | 0.72 | no obvious floating oil | slight floating oil | slight layer-separation | obvious layer-separation, demulsification |
| Comparative Example 3 | 0.65 | no obvious floating oil | slight floating oil | slight layer-separation | obvious layer-separation, demulsification |

From the results of the stability constants in Table 1, it can be seen that the stability constants of Examples 1 to 5 are significantly smaller than the Comparative Examples. The initial emulsions of Examples 1-5 can be kept stable for 40 min, and slight floating oil appeared after 60 min. In the initial emulsions of Comparative Examples 1 to 3, there was slight floating oil after the initial emulsions were placed for 30 min, there was slight layer-separation after 40 min, and obvious layer-separation and demulsification occurred after 60 min. It is shown that the emulsification effect and stability of the initial emulsion can be significantly increased by using the improved formulations and emulsification method of the present invention.

Experimental Example 2: Determination of Key Quality Indicators and Entrapment Efficiency of Finished Products The national drug standard of flurbiprofen axetil injection (YBH15412004-2014Z) is referred for the limit requirements of the main physical and chemical indicators of the product. Since the methoxyaniline value and the peroxide value represent the aldehydes and ketones produced by the oxidation of oils and fats (soybean oil, and egg yolk lecithin), which are harmful to the human liver, these values should be controlled by referring to the import standard of propofol fat emulsion injection. The distribution of drug emulsion particles and drug entrapment efficiency are key indicators of drug-loaded liposomes and drug-loaded emulsions, and are important factors affecting the targeted distribution and efficacy of drug-loaded emulsions. The General Regulation 9014 of the Fourth Edition of the Chinese Pharmacopoeia 2015 stipulates that the entrapment efficiency of drug-loaded microparticle formulations should generally not be lower than 80%.

Figure 2:
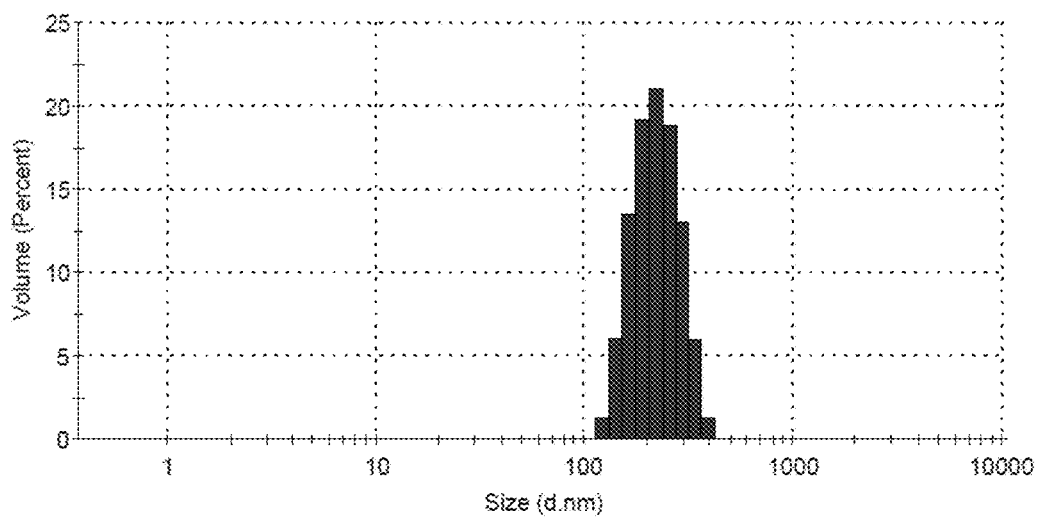
FIG. 2 is a particle size distribution diagram of the flurbiprofen axetil emulsion for injection provided in Example 2 of the present invention.
Figure 3:
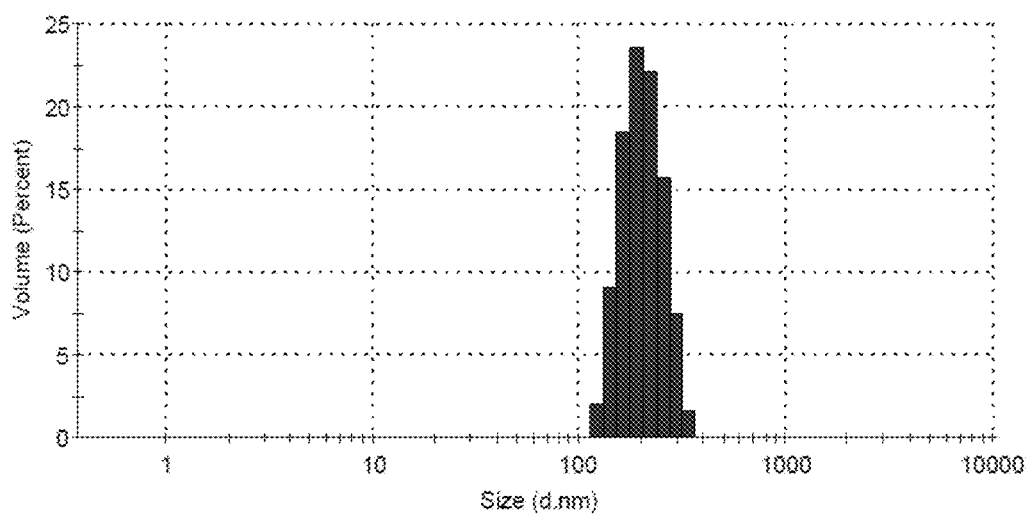
FIG. 3 is a particle size distribution diagram of the flurbiprofen axetil emulsion for injection provided in Example 3 of the present invention.
Figure 4:
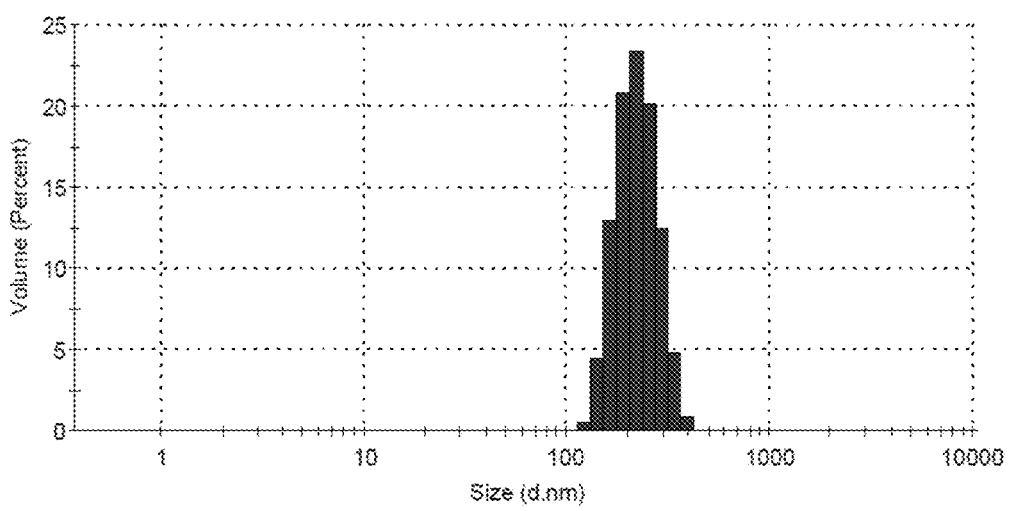
FIG. 4 is a particle size distribution diagram of the flurbiprofen axetil emulsion for injection provided in Example 4 of the present invention.
Figure 5:
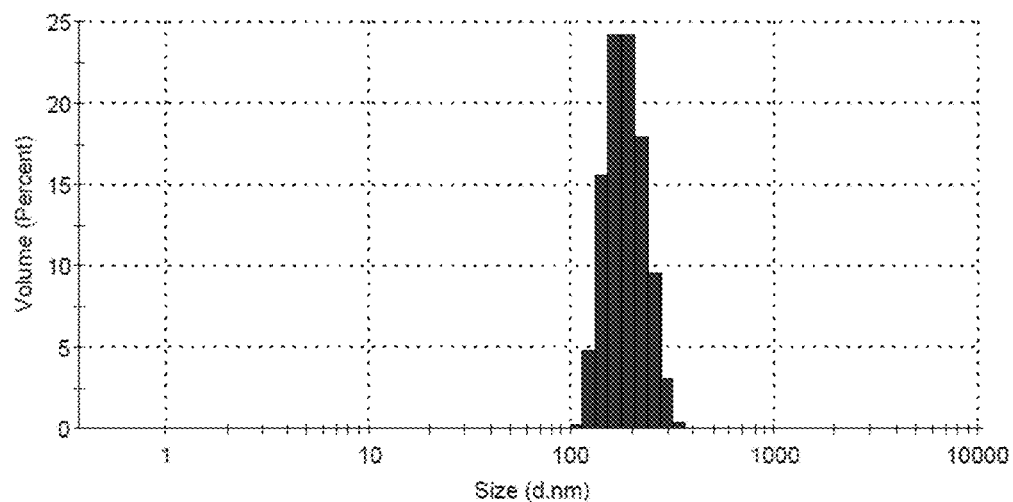
FIG. 5 is a particle size distribution diagram of a flurbiprofen axetil emulsion for injection provided in Example 5 of the present invention.
Figure 6:
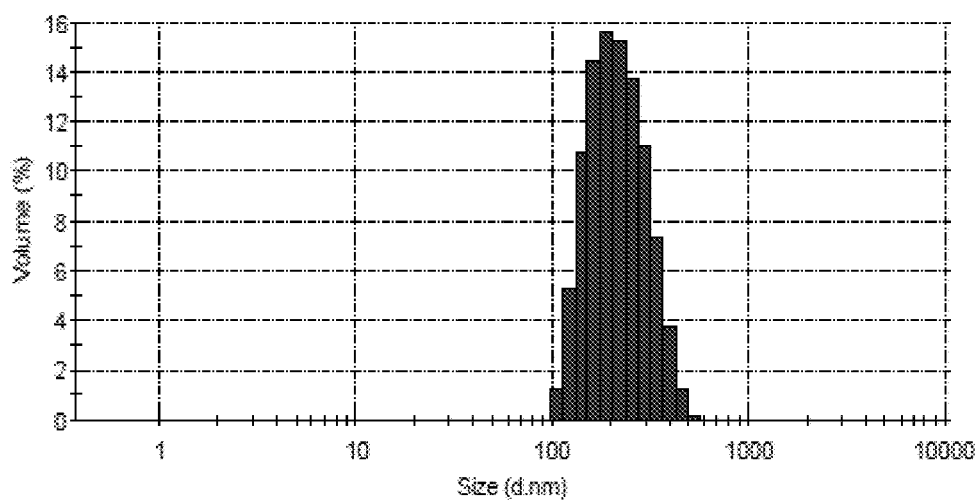
FIG. 6 is a particle size distribution diagram of the flurbiprofen axetil emulsion for injection provided by Comparative Example 1 of the present invention.
Figure 7:
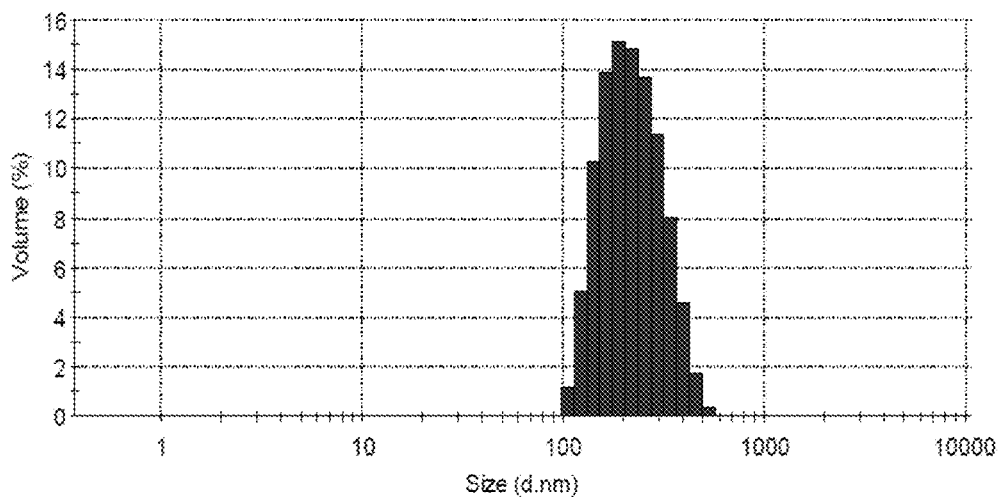
FIG. 7 is a particle size distribution diagram of the flurbiprofen axetil emulsion for injection provided by Comparative Example 2 of the present invention.
Figure 8:
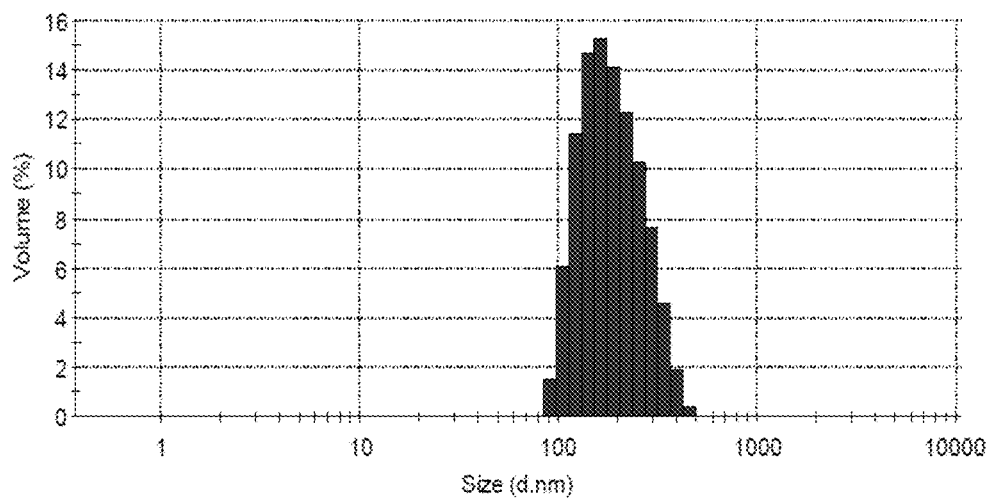
FIG. 8 is a particle size distribution diagram of the flurbiprofen axetil emulsion for injection provided by Comparative Example 3 of the present invention.

Appearance, pH value, peroxide value, methoxyaniline value, content of flurbiprofen, and entrapment efficiency of the flurbiprofen axetil emulsion for injection (Examples 1 to 5 and Comparative Examples 1 to 3) of the present invention were measured. The measurement results were shown in Table 2. The distributions of emulsion particles were shown in FIGS. 1 to 8.

Measurement method of particle size distribution of emulsion particles: The particle size of the flurbiprofen axetil emulsion for injection prepared in the present invention (Examples 1 to 5 and Comparative Examples 1 to 3) was measured by using a dynamic light scattering particle size analyzer (Z590, Malvern, UK) to obtain the particle size distribution of the flurbiprofen axetil emulsion for injection.

Measurement method of methoxyaniline value: 10 ml of the inventive product was precisely measured, and was placed into a 250 ml round bottom flask. 20 ml of absolute ethanol was added, and water was removed by vacuum rotary evaporation in a water bath at 60° C. The residue was dissolved in an isopropanol-isooctane (20:80) solution and transferred to a 25 ml volumetric flask. The above isopropanol-isooctane solution was added to dilute to the scale mark, followed by shaking, and filtering, and the filtrate was used as the test solution. The absorbance (A1) of the test solution was measured according to the ultraviolet-visible spectrophotometry (General Regulation 0401 of the Fourth Edition of the Chinese Pharmacopoeia 2015). 5 ml of the test solution and 5 ml of isopropanol-isooctane (20:80) solution were precisely measured, and 1 ml of 0.25% 4-methoxyaniline in glacial acetic acid solution (newly prepared for temporary use) was precisely added into each solution. The absorbance (A2) of the test solution was measured at a wavelength of 350 nm. The methoxyaniline value was calculated according to the following formula, and the methoxyaniline value of the inventive product should not exceed 10.0.

$$\text{Methoxyaniline value} = \frac{25 \times (1.2 \times A_2 - A_1)}{V \times B}$$

wherein: V is the sampling volume of the sample, ml;
B is the labeled amount of soybean oil in the sample, g/ml;
1.2 is the dilution factor of the solution after adding 0.25% 4-methoxyaniline in glacial acetic acid solution.

Measurement method of peroxide value: 10 ml of the inventive product was precisely measured, and was placed into a 250 ml iodine bottle. 40 ml of chloroform-glacial acetic acid (2:3) mixed solution was added, and shaken gently. 0.5 ml of saturated potassium iodide solution was precisely added, and sealed, then 30 ml of water was added, the resultant was titrated with sodium thiosulfate titration solution (0.01 mol/L), and fully shaken until the yellow color almost disappeared. 4 ml of starch indicator solution was added for continuous titration, and the resultant was fully shaken until the blue color disappeared. The number of milliliters of sodium thiosulfate titration solution (0.01 mol/L) consumed by the test product should not exceed 1.0 ml.

Measurement method of entrapment efficiency: The absorbance of the entrapped drug test solution and the total drug test solution were measured at 254 nm according to the ultraviolet-visible spectrophotometry (General Regulation 0401 of the Fourth Edition of the Chinese Pharmacopoeia 2015). The entrapment efficiency was calculated according to the following formula.

Calculation formula: Entrapment efficiency (%)=Absorbance of entrapped drug×100% Absorbance of total drug Entrapped drug test solution: 0.2 ml of the inventive product was precisely measured, and was added to the top of the Sephadex G-50 gel column. Water for injection was used as the eluent, and the flow rate was 0.5 ml/min. The eluate flowing out was collected with an automatic collector, 1 ml per tube, and the eluate in the $10^{th}$-$20^{th}$ tube was taken and put into a 100 ml volumetric flask, and the test tube was washed several times with absolute ethanol. The washing solution was added into the volumetric flask, and absolute ethanol was added to dilute to the scale mark, and the resultant was shaken evenly to obtain the entrapped drug test solution.

Total drug test solution: 0.2 ml of the inventive product was precisely measured, and was added into a 100 ml volumetric flask. Absolute ethanol was added to dilute to the scale mark, and the resultant was shaken evenly to obtain the total drug test solution.

nificantly reduced, the distribution of the finished emulsion particles is more uniform, and it is easier to target and gather in the wounded tissue after entering the body. It is shown that the combination of the continuous emulsification method of the present invention and the addition of a stabilizer can significantly improve the emulsification effect of the inventive product, improve the drug entrapment efficiency, reduce the degradation of the main drug and auxiliary materials, and significantly improve the product quality.

Experimental Example 3: Tissue Distribution Test

The flurbiprofen axetil emulsions for injection prepared in Example 1 and Comparative Example 1 were selected, and the rat with surgery trauma was used as a model to investigate the tissue distribution characteristics in vivo.

Test method: Thirty SD rats (one half is male and the other half is female) with surgical trauma were selected, and were randomly assigned to the example group and the comparative example group with 15 rats in each group. The flurbiprofen axetil emulsions for injection prepared in Example 1 and Comparative Example 1 were selected. In the example group and the comparative example group, the dose for rat was converted into 5 mg·kg$^{-1}$ according to the clinical dosage for human. The tail vein injection was carried out. In the example group and the comparative example group, 5 rats were taken 30 minutes, 2 hours and 4 hours after administration, respectively, blood samples were collected from the femoral vein, and serum was taken after centrifugation. The animals were sacrificed by dislocation, and then

TABLE 2

Comparison results of key quality indicators of the examples and comparative examples

| Test items | Limit requirements | Example 1 | Example 2 | Example 3 | Example 4 | Example 5 | Comparative Example 1 | Comparative Example 2 | Comparative Example 3 |
|---|---|---|---|---|---|---|---|---|---|
| Appearance | White uniform emulsion | White emulsion | White emulsion | White emulsion | White emulsion | White emulsion | White emulsion with oil droplets on the surface | White emulsion | White emulsion |
| pH value | 4.5-6.5 | 6.1 | 6.2 | 6.1 | 6.3 | 6.2 | 6.1 | 6.2 | 6.2 |
| Methoxyaniline value | should not exceed 6.0 | 1.6 | 1.8 | 2.1 | 1.7 | 1.9 | 4.2 | 4.1 | 3.8 |
| Peroxide value (meq/L) | should not exceed 2.0 | 0.08 | 0.10 | 0.12 | 0.11 | 0.10 | 0.38 | 0.45 | 0.42 |
| Flurbiprofen (mg/ml) | should not exceed 0.74 mg/ml | 0.08 | 0.09 | 0.09 | 0.09 | 0.07 | 0.25 | 0.28 | 0.24 |
| Average particle size | should not exceed 400 nm | 188 nm | 194 nm | 189 nm | 206 nm | 192 nm | 258 nm | 247 nm | 260 nm |
| Cumulative value of 90% particle size | should not exceed 600 nm | 286 nm | 305 nm | 296 nm | 315 nm | 288 nm | 385 nm | 370 nm | 369 nm |
| Entrapment efficiency (%) | should not less than 80% | 96.4% | 97.2% | 96.8% | 97.5% | 98.0% | 90.4% | 91.0% | 90.8% |
| Content | 90%-110% | 101.2% | 100.8% | 101.5% | 100.4% | 100.6% | 99.4% | 98.5% | 99.0% |

As shown in the results of Table 2, as compared with Comparative Examples 1-3, the appearance of the flurbiprofen axetil emulsion for injection prepared in Examples 1-5 are better, the entrapment efficiency of the finished product is significantly increased, the contents of the related substances (flurbiprofen) and the oxidation products of auxiliary materials (methoxyaniline value, peroxide value) are sigthe heart, liver, spleen, lung, kidney and wounded muscle were collected. After the organs and tissues were rinsed with normal saline and the water was sucked dry, 0.5 g of each organ or tissue were taken respectively, and 1.5 ml of normal saline was added to homogenize. After pretreatment, the concentrations of flurbiprofen (an active metabolite) in each organ or tissue and serum were determined by HPLC.

TABLE 3

Comparison results of tissue distribution of the Examples and Comparative Examples sampling time (h) - average drug concentration in each tissue (n = 5, μg/g)

| Tissue | 0.5 h | | 2 h | | 4 h | |
|---|---|---|---|---|---|---|
| | Example 1 | Comparative Example 1 | Example 1 | Comparative Example 1 | Example 1 | Comparative Example 1 |
| Heart | 3.61 | 3.05 | 3.12 | 1.95 | 1.48 | 1.92 |
| Liver | 5.95 | 5.33 | 4.01 | 4.74 | 1.67 | 1.65 |
| Spleen | 3.90 | 3.24 | 2.01 | 2.13 | 0 | 0.44 |
| Lung | 8.11 | 7.44 | 5.60 | 4.68 | 1.85 | 2.16 |
| Kidney | 3.63 | 4.26 | 2.05 | 2.86 | 1.74 | 1.91 |
| Muscle | 2.25 | 1.86 | 1.18 | 1.52 | 0.62 | 0.65 |
| Wounded muscle | 7.62 | 5.04 | 5.67 | 3.36 | 2.38 | 1.39 |
| Serum | 20.40 | 22.29 | 13.21 | 18.17 | 10.77 | 10.88 |

As shown in the results of Table 3, the distribution concentrations in heart, liver, spleen, lung, kidney, and muscle of the example group at 0.5 h are all higher than those of the comparative example group, and decreased rapidly at 2 h and 4 h. The concentrations of the example groups at 4 h are not higher than those of the comparative group, wherein the concentration distribution in the spleen of the example group is significantly lower than that of the comparative example group ($P<0.05$), indicating that the test formulation does not accumulate in major organs. At different time points after administration, the drug concentration in the wounded muscle of the example group is 3 to 5 times that of the normal muscle, and the drug concentration in the wounded muscle of the comparative example group was 2 to 3 times that of the normal muscle. It is shown that the flurbiprofen axetil emulsion for injection prepared by the present invention increases the drug entrapment efficiency, the emulsion particles have more uniform distribution, and the drug is better targeted to the wounded tissue, which is helpful to improve the drug efficacy. The results of the flurbiprofen axetil emulsions for injection obtained in Examples 2 to 5 are similar to or even better than those of the flurbiprofen axetil emulsion for injection obtained in Example 1.

Finally, the method of the present invention is only a preferred embodiment, and is not intended to limit the protection scope of the present invention. Any modification, equivalent replacement, or improvement made within the spirit and principle of the present invention shall be included in the protection scope of the present invention.

INDUSTRIAL APPLICABILITY

The present invention provides a flurbiprofen axetil emulsion for injection and a preparation method thereof. The flurbiprofen axetil emulsion for injection is prepared by the following method: under the protection of nitrogen gas, an oil phase is added to a water phase in a stepwise manner to perform shear mixing to obtain an initial emulsion; the stepwise manner is specifically as follows: 40 wt % to 60 wt % of an oil phase based on the total oil phase is added to a water phase to perform shear mixing for 10 min to 30 min to obtain a crude emulsion A; 20 wt % to 30 wt % of an oil phase based on the total oil phase is added to the crude emulsion A to perform shear mixing for 10 min to 30 min to obtain a crude emulsion B; and the crude emulsion B is mixed with the rest of the total oil phase to perform shear mixing for 10 min to 30 min; the oil phase includes flurbiprofen axetil, an oil phase solvent, an emulsifier, and a stabilizer, and the water phase includes water for injection and/or an osmotic pressure regulator. In the presence of a stabilizer in the oil phase, the present invention can effectively improve the emulsification effect by using the stepwise emulsifying technique for the oil phase, so that the obtained flurbiprofen axetil emulsion for injection has more uniform particle size, higher drug entrapment efficiency, and better targeting of the drug to the wounded tissue, and has good economic value and application prospects.

What is claimed is:

1. A method of preparation of a flurbiprofen axetil emulsion for injection, comprising:
   adding 40 wt % to 60 wt % of an oil phase based on the total oil phase to a water phase with shear mixing under protection of nitrogen gas for 10 min to 30 min to obtain a crude emulsion A;
   adding 20 wt % to 30 wt % of the oil phase based on the total oil phase to the crude emulsion A with shear mixing under the protection of the nitrogen gas for 10 min to 30 min to obtain a crude emulsion B; and
   mixing the crude emulsion B with the rest of the total oil phase with shear mixing under the protection of the nitrogen gas for 10 min to 30 min to obtain an initial emulsion;
   wherein the oil phase comprises flurbiprofen axetil, an oil phase solvent, an emulsifier, and a stabilizer, and
   wherein the water phase comprises water for injection optionally an osmotic pressure regulator,
   wherein the oil phase solvent is selected from the group consisting of a refined soybean oil, olive oil, medium-chain triglyceride, and a combination thereof,
   wherein the emulsifier is selected from the group consisting of egg yolk lecithin, soybean lecithin, polyethylene glycol glyceryl stearate, and a combination thereof,
   wherein the stabilizer is selected from the group consisting of dioleoylphosphatidylserine, dipalmitoylphosphatidic acid, sphingomyelin, and a combination thereof.

2. The method according to claim 1, comprising:
   wherein the crude emulsion A is obtained by adding 45 wt % to 55 wt % of the oil phase based on the total oil phase to the water phase with shear mixing under the protection of the nitrogen gas for 10 min to 20 min;
   wherein the crude emulsion B is obtained by adding 20 wt % to 30 wt % of the oil phase based on the total oil phase to the crude emulsion A with shear mixing under the protection of the nitrogen gas for 10 min to 20 min; and wherein the crude emulsion B is mixed with the rest of the total oil phase with shear mixing under the protection of the nitrogen gas for 20 min to 30 min.

3. The method according to claim 1, wherein, the shear mixing speed is in the range of 4000 rpm to 10000 rpm.

4. The method according to claim 3:
wherein the crude emulsion A is obtained with shear mixing at 4000 rpm to 6000 rpm;
wherein the crude emulsion B is obtained with shear mixing at 6000 rpm to 8000 rpm;
wherein the crude emulsion B is mixed with the rest of the total oil phase with shear mixing at 8000 rpm to 10000 rpm.

5. The method according to claim 1, wherein the flurbiprofen axetil emulsion for injection comprises the following components: 1% to 2% of flurbiprofen axetil, 8% to 12% of an oil phase solvent, 1.0% to 1.5% of an emulsifier, 0.01% to 0.1% of a stabilizer, and the rest is water.

6. The method according to claim 1, wherein the flurbiprofen axetil emulsion for injection includes 2.0% to 3.0% of the osmotic pressure regulator.

7. The method according to claim 6, wherein the osmotic pressure regulator is one or two selected from the group consisting of glycerol, sucrose, and mannitol.

8. The method according to claim 1, further comprising:
adjusting pH of the initial emulsion to 6.0 to 7.0,
homogenizing under a pressure of 60 Mpa to 100 Mpa and a temperature of 10° C. to 40° C. for 3 to 5 times to obtain a semi-finished product;
subjecting the obtained semi-finished product to filtration, filling,
sealing and
sterilizing to obtain the flurbiprofen axetil emulsion for injection.

9. The method according to claim 1, wherein the stabilizer is dioleoylphosphatidylserine.

10. The method according to claim 1, wherein the emulsifier is egg yolk lecithin.

11. The method of preparation according to claim 1, wherein the osmotic pressure regulator is selected from the group consisting of glycerol, sucrose, mannitol, and a combination thereof.

* * * * *